US00PP13090P2

(12) United States Plant Patent
Vandenberg et al.

(10) Patent No.: US PP13,090 P2
(45) Date of Patent: Oct. 15, 2002

(54) CHRYSANTHEMUM PLANT NAMED 'ROYAL NEW YOORLEANS'

(75) Inventors: Cornelis P. Vandenberg, Salinas, CA (US); Wendy R. Bergman, Lehigh Acres, FL (US)

(73) Assignee: Yoder Brothers, Inc., Barberton, OH (US)

( * ) Notice: Subject to any disclaimer, the term of this patent is extended or adjusted under 35 U.S.C. 154(b) by 1 days.

(21) Appl. No.: 09/829,492

(22) Filed: Apr. 11, 2001

(51) Int. Cl.[7] ..... A01H 5/00
(52) U.S. Cl. ..... Plt./286
(58) Field of Search ..... Plt./286, 297, 298

(56) References Cited

U.S. PATENT DOCUMENTS 4,616,099 A * 10/1986 Sparkes ..... 47/58

OTHER PUBLICATIONS

Shukla, et al., 1993, "Mutation studies on early and late varieties of garden chrysanthemums", J. Nuclear Agric. Biol., 22 (3–4): 138–142.*

Broertjes, et al., 1980, "A mutant of a mutant of a . . . Irradiation of progrossive radiation induced mutants in a mutation breeding programme with *Chrysanthemum morifolium*", Euphytica, 29: 525–530.*

Gosling, ed., 1979, "The Chrysanthemum Manual—6$^{th}$ edition", The National Chrysanthemum Society, London, Essex Telegraph Press, Ltd., pp. 329–336.*

Broertjes, et al., 1978, "Application of Mutation Breeding Methods in the Improvement of Vegetatively Propagated Crops", Elsevier Sci. Pub. Co., New York, pp. 162–175.*

Searle, et al., 1968, "Chrysanthemums the Year Round", Blanford Press, London, pp. 27–29, 320–327.*

Chan, 1966, "Chrysanthemum and rose mutations induced by x–rays", Am. Soc. Hort. Sci. Proc., pp. 613–620.*

Broertjes, 1966, "Mutation breeding of chrysanthemums", Euphytica, 15:156–162.*

Dowrick, et al., 1966, "The induction of mutations in chrysanthemum using x– and gamma radiation", Euphytica, 15:204–210.*

* cited by examiner

*Primary Examiner*—Howard J. Locker
(74) *Attorney, Agent, or Firm*—C. A. Whealy

(57) ABSTRACT

A distinct cultivar of Chrysanthemum plant named 'Royal New Yoorleans', characterized by its uniform and upright plant habit; strong and vigorous growth habit; dark green foliage; uniform flowering response; early and freely flowering habit; daisy-type inflorescences; purple and white bi-colored ray florets and bright yellow-colored disc florets; and good postproduction longevity.

2 Drawing Sheets

BACKGROUND OF THE INVENTION

The present Invention relates to a new and distinct cultivar of Chrysanthemum plant, botanically known as *Chrysanthemum×morifolium* and hereinafter referred to by the name 'Royal New Yoorleans'.

The new Chrysanthemum is a product of a planned breeding program conducted by the Inventors in Fort Myers, Fla. and Salinas, Calif. The objective of the breeding program is to create new potted Chrysanthemum cultivars that are suitable for year-round production with uniform plant growth habit, good vigor, desirable inflorescence form and floret colors, fast response time, and good postproduction longevity.

The new Chrysanthemum is a naturally-occurring whole plant mutation of a proprietary induced mutation that originated by exposing unrooted cuttings of the Chrysanthemum cultivar New Yoorleans, disclosed in U.S. Plant Pat. No. 11,215, to X-ray radiation in December, 1996, in Fort Myers, Fla. The new Chrysanthemum was discovered and selected by the Inventors as a single flowering plant within a population of plants of the irradiated selection in April, 1997 in Salinas, Calif. The selection of this plant was based on its uniform plant growth habit, good vigor, desirable inflorescence form and floret colors, fast response time, and good postproduction longevity.

Asexual reproduction of the new Chrysanthemum by vegetative tip cuttings was first conducted in Salinas, Calif. in July, 1997. Asexual reproduction by cuttings has shown that the unique features of this new Chrysanthemum are stable and reproduced true to type in successive generations.

SUMMARY OF THE INVENTION

The cultivar Royal New Yoorleans has not been observed under all possible environmental conditions. The phenotype may vary somewhat with variations in environment such as temperature, daylength, and/or light level, without, however, any variance in genotype.

The following traits have been repeatedly observed and are determined to be the unique characteristics of 'Royal New Yoorleans'. These characteristics in combination distinguish 'Royal New Yoorleans' as a new and distinct Chrysanthemum:

1. Uniform and upright plant habit.
2. Strong and vigorous growth habit.
3. Dark green foliage.
4. Uniform flowering response.

5. Typically grown as a spray-type.

6. Early flowering, eight-week response time.

7. Freely flowering habit.

8. Daisy-type inflorescences that are about 6.3 cm in diameter.

9. Purple and white bi-colored ray florets and bright yellow-colored disc florets.

10. Good postproduction longevity with plant maintaining good substance and color for at least three weeks in an interior environment.

Plants of the new Chrysanthemum can be compared to plants of the cultivar New Yoorleans. In side-by-side comparisons conducted by the Inventors in Salinas, Calif., plants of the New Chrysanthemum differ from plants of the cultivar New Yoorleans in the following characteristics:

1. Ray florets of plants of the new Chrysanthemum have a larger ratio of purple to white coloration than ray florets of plants of the cultivar New Yoorleans.

2. Purple ray floret color of plants of the new Chrysanthemum is darker than purple ray floret color of plants of the cultivar New Yoorleans.

3. Retention of ray floret coloration under high temperature and/or low light conditions is better on plants of the new Chrysanthemum than plants of the cultivar New Yoorleans.

BRIEF DESCRIPTION OF THE PHOTOGRAPHS

The accompanying colored photographs illustrate the overall appearance of the new Chrysanthemum showing the colors as true as it is reasonably possible to obtain in colored reproductions of this type. Colors in the photographs may differ from the color values cited in the detailed botanical description which accurately describe the colors of the new Chrysanthemum.

The photograph on the first sheet comprises a side perspective view of a typical flowering plant of 'Royal New Yoorleans' grown a spray-type.

The photograph at the top of the second sheet comprises a close-up view of typical inflorescences of 'Royal New Yoorleans' grown as a spray-type.

The photograph at the bottom of the second sheet comprises a close-up view of typical inflorescences of the new Chrysanthemum (left) and 'New Yoorleans' (right).

DETAILED BOTANICAL DESCRIPTION

In the following description, color references are made to The Royal Horticultural Society Colour Chart except where general terms of ordinary dictionary significance are used. The following observations and measurements describe plants grown and flowered during the winter in Salinas, Calif., in a fiberglass-covered greenhouse and under conditions which approximate those generally used in commercial potted Chrysanthemum production. During the production of these plants, the following conditions were measured: day temperatures, 21 to 27° C.; night temperatures, 17 to 19° C.; and light levels, 5,000 to 6,000 foot-candles. Four unrooted cuttings were directly stuck in 15-cm containers, exposed to long day/short night conditions, and pinched once about 14 days later. At that time, the photoinductive short day/long night treatments were started. Plants used for this description were grown as spray-types. Measurements and numerical values represent averages of typical flowering plants.

Botanical classification: *Chrysanthemum×morifolium* cultivar Royal New Yoorleans.

Commercial classification: Daisy-type potted Chrysanthemum.

Parentage: Naturally-occurring whole plant mutation of a proprietary *Chrysanthemum×morifolium* induced mutation, not patented.

Propagation:

*Type.*—Terminal tip cuttings.

*Time to initiate roots.*—About four days at 21° C.

*Time to produce a rooted cutting.*—About ten days at 21° C.

*Root description.*—White, fibrous.

*Rooting habit.*—Freely branching.

Plant description:

*Appearance.*—Herbaceous daisy-type potted Chrysanthemum typically grown as a spray-type. Stems mostly upright and somewhat outwardly spreading; uniform crown. Freely branching, about three lateral branches develop after removal of terminal apex (pinching); dense and full plant. Vigorous.

*Plant height.*—About 28.5 cm.

*Plant width.*—About 37 cm.

*Lateral branches.*—Length: About 23 cm. Diameter: About 4 mm. Internode length: About 1.75 cm. Strength: Strong. Texture: Pubescent. Color: 146A.

*Foliage description.*—Arrangement: Alternate. Quantity of leaves per lateral stem: About 11 or 12. Length: About 6.9 cm. Width: About 6.1 cm. Apex: Rounded, cuspidate to mucronate. Base: Attenuate to truncate. Margin: Palmately lobed, sinuses between lateral lobes parallel to divergent. Texture: Upper and lower surfaces with very fine pubescence: veins prominent on lower surface. Color: Young foliage, upper surface: Darker than 147A. Young foliage, lower surface: Darker than 147B. Mature foliage, upper surface: Close to 147A. Mature foliage, lower surface: Close to 147B. Venation, upper surface: Close to 146C. Venation, lower surface: 147B to 146C. Petiole length: About 2.1 cm. Petiole diameter: About 3.5 mm. Petiole color: Close to 146C.

Inflorescence description:

*Appearance.*—Daisy-type inflorescence form with elongated oblong-shaped ray florets. Inflorescences borne on terminals above foliage. Disk and ray florets arranged acropetally on a capitulum. Not fragrant. Typically grown as a natural or center-budded spray-type.

*Flowering response.*—Under natural conditions, plants flower in the autumn/winter in the Northern Hemisphere. At other times of the year, inflorescence initiation and development can be induced under short day/long night conditions (at least 13.5 hours of darkness). Early flowering; plants exposed to two weeks of long day/short night conditions followed by photoinductive short day/long night conditions flower about 50 to 55 days later when grown during the winter.

*Postproduction longevity.*—Inflorescences maintain good color and substance for at least three weeks in an interior environment.

*Quantity of inflorescences.*—Freely flowering, about 9 inflorescences develop per lateral stem, or about 27 inflorescences per plant.

*Inflorescence bud.*—Height: About 7 mm. Diameter: About 9 mm. Color: Close to 137A.

*Inflorescence size*.—Diameter: About 6.3 cm. Depth (height): About 1.8 cm. Diameter of disc: About 1.6 cm. Receptacle diameter: About 6 mm.

*Ray florets*.—Shape: Elongated-oblong. Orientation: Initially upright, then about 70° from vertical. Aspect: Mostly flat and straight. Length: About 3.2 cm. Width: About 1.2 cm. Corolla tube length: About 2 mm. Apex: Acute. Base: Attenuate; short corolla tube. Margin: Entire. Texture: Smooth, glabrous, satiny. Number of ray florets per inflorescence: About 23 arranged in one or two rows. Color: When opening and fully expanded, upper surface: Apex and mid-section: Closest to 61A. Base: 155D. When opening and fully expanded, lower surface: Apex to center: 155D underlain with 71A. Base to center: 155D.

*Disc florets*.—Arrangement: Massed at center of receptacle. Shape: Tubular, elongated. Apex: Five-pointed. Length: About 6 mm. Width: Apex: About 1.5 mm. Base: About 1 mm. Number of disc florets per inflorescence: About 144. Color: Immature: 154A to 5A. Mature: Apex: 7A. Mid-section: Close to 145C. Base: 155D.

*Peduncles*.—Length: First peduncle: About 3.2 cm. Fourth peduncle: About 5.3 cm. Seventh peduncle: About 5.7 cm. Diameter: About 2 mm. Angle to vertical: About 45 to 50° from vertical. Strength: Moderately strong, flexible. Texture: Pubescent. Color: 146A.

*Reproductive organs*.—Androecium: Present on disc florets only. Anther color: 9A. Pollen: Not observed. Gynoecium: Present on both ray and disc florets.

*Seed*.—Seed production has not been observed.

Disease resistance: Resistance to pathogens common to Chrysanthemums has not been observed on plants grown under commercial greenhouse conditions.

It is claimed:

1. A new and distinct cultivar of Chrysanthemum plant named 'Royal New Yoorleans', as illustrated and described.

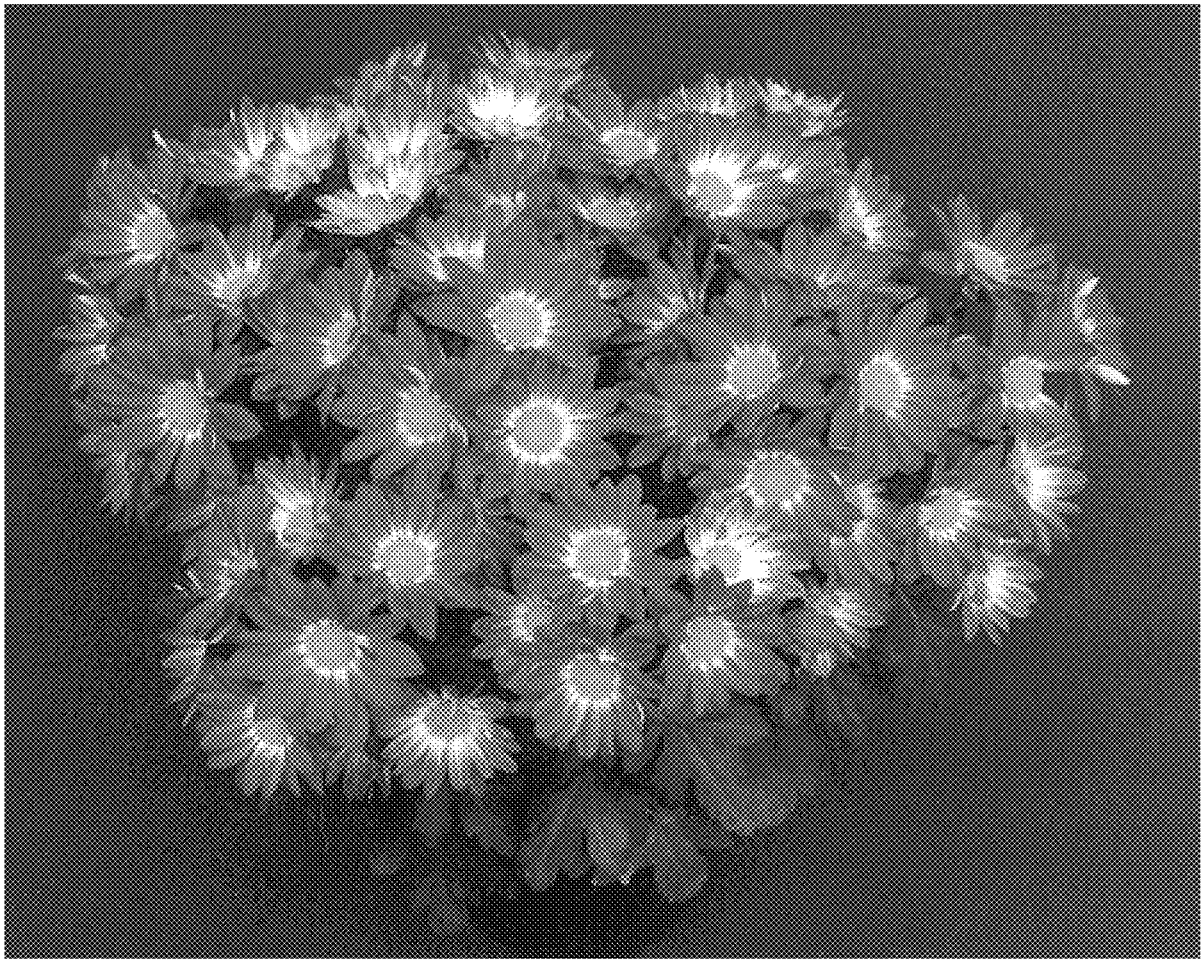

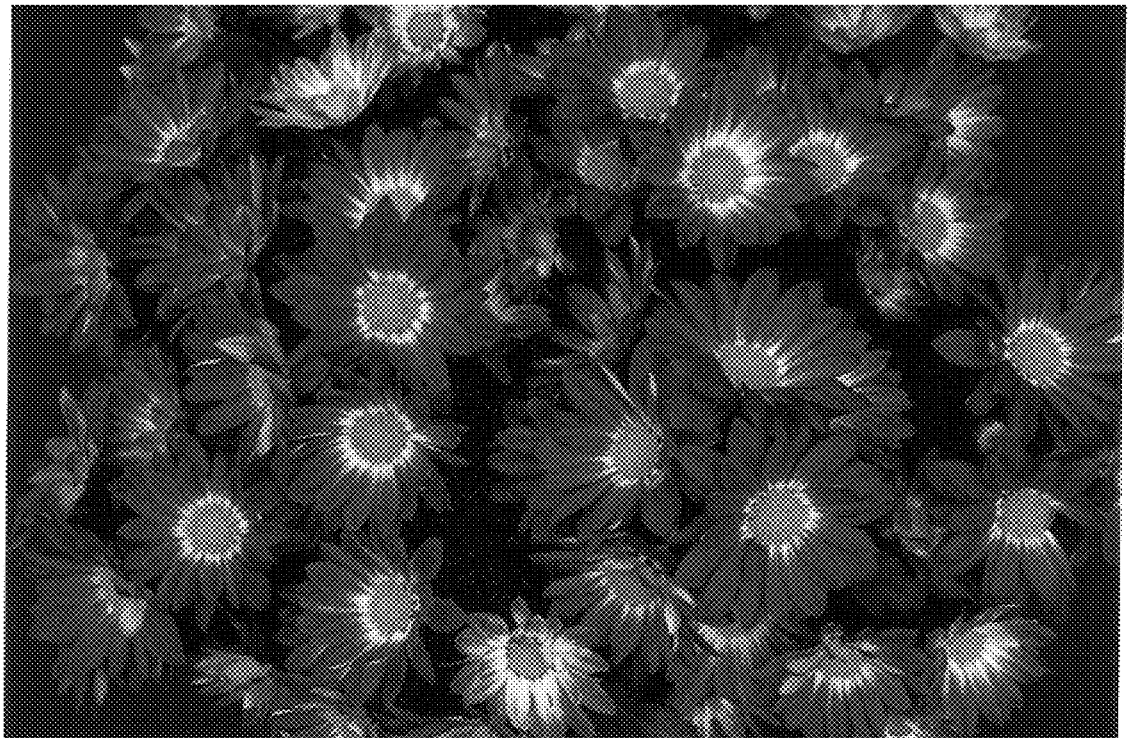
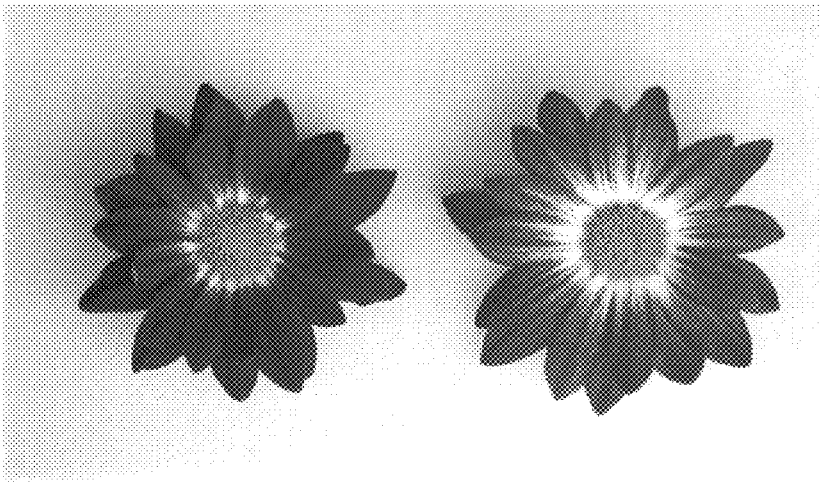

* * * * *